United States Patent [19]

Clement

[11] Patent Number: 5,197,968

[45] Date of Patent: Mar. 30, 1993

[54] DISPOSABLE TISSUE RETRIEVAL ASSEMBLY

[75] Inventor: Thomas P. Clement, Bloomington, Ind.

[73] Assignee: Mectra Labs, Inc., Bloomfield, Ind.

[21] Appl. No.: 745,252

[22] Filed: Aug. 14, 1991

[51] Int. Cl.$^5$ ............................. A61B 17/00; A61B 17/36
[52] U.S. Cl. ......................................... 606/115; 606/110;
606/113; 606/114; 606/127; 606/128; 604/22;
604/32; 604/93; 604/119; 604/128; 604/902
[58] Field of Search ................ 606/127, 128, 159, 167,
606/170, 171, 181, 182, 184, 185, 115, 110, 113,
114; 604/53, 22, 32, 35, 93, 119, 128, 902

[56] References Cited

U.S. PATENT DOCUMENTS

| | | |
|---|---|---|
| 811,111 | 1/1906 | Wegefarth . |
| 2,943,626 | 7/1960 | Dormia ............................ 606/127 |
| 3,916,909 | 11/1975 | Kletschka et al. . |
| 4,002,169 | 1/1977 | Cupler . |
| 4,046,149 | 9/1977 | Komiya ............................ 606/127 |
| 4,046,150 | 9/1977 | Schwartz et al. . |
| 4,198,960 | 4/1980 | Utsugi ............................ 606/127 |
| 4,203,429 | 5/1980 | Vasilevsky et al. ............... 606/128 |
| 4,227,532 | 10/1980 | Bluhm et al. .................... 606/128 |
| 4,243,040 | 1/1981 | Beecher . |
| 4,299,217 | 11/1981 | Sagae et al. . |
| 4,509,517 | 4/1985 | Zibelin . |
| 4,611,594 | 9/1986 | Corayhack et al. ............... 606/128 |
| 4,612,931 | 9/1986 | Dormia ............................ 606/127 |
| 4,625,726 | 12/1986 | Duthey ............................ 606/127 |
| 4,633,871 | 1/1987 | Shinozuka ........................ 606/127 |
| 4,667,927 | 5/1987 | Oscarsson . |
| 4,741,335 | 5/1988 | Okada ............................ 606/127 |
| 4,790,812 | 12/1988 | Hawkins, Jr. et al. . |
| 4,807,626 | 2/1989 | McGirr . |
| 4,811,735 | 3/1989 | Nash et al. . |
| 4,898,574 | 2/1990 | Uchiyama et al. ............... 606/127 |
| 4,927,426 | 5/1990 | Dretler ............................ 606/128 |
| 4,997,435 | 3/1991 | Demeter . |
| 5,019,054 | 5/1991 | Clement et al. .................... 604/32 |

Primary Examiner—Stephen C. Pellegrino
Assistant Examiner—Glenn K. Dawson
Attorney, Agent, or Firm—Barnes & Thornburg

[57] ABSTRACT

The present invention provides an apparatus for retrieval, dissection and removal of small organs and tissue from a patient's body. The instrument includes a collapsible basket defining a basket cavity. An anvil is attached to the distal end of the basket to form an impacting surface. A cutting cannula defining a cutting cavity is positioned to be reciprocatingly movable to pass through the basket cavity and impact the anvil. The cutting cannula is manually and reciprocatingly driven to pass into and through the basket cavity, cutting any tissue contained in the basket cavity. The cut tissue is then suctioned from the body for analysis.

20 Claims, 3 Drawing Sheets

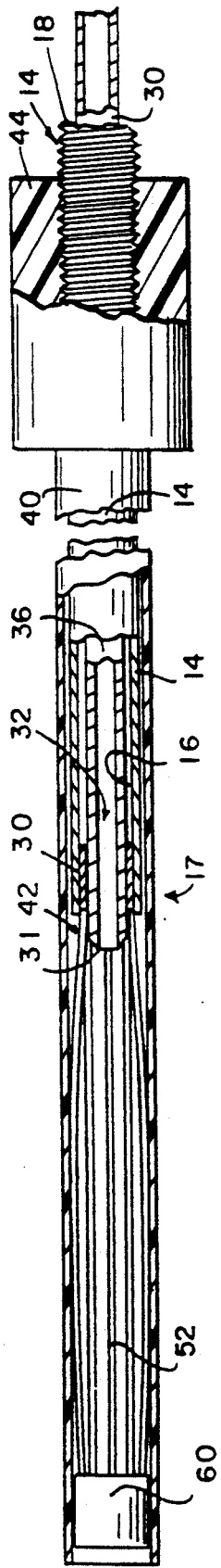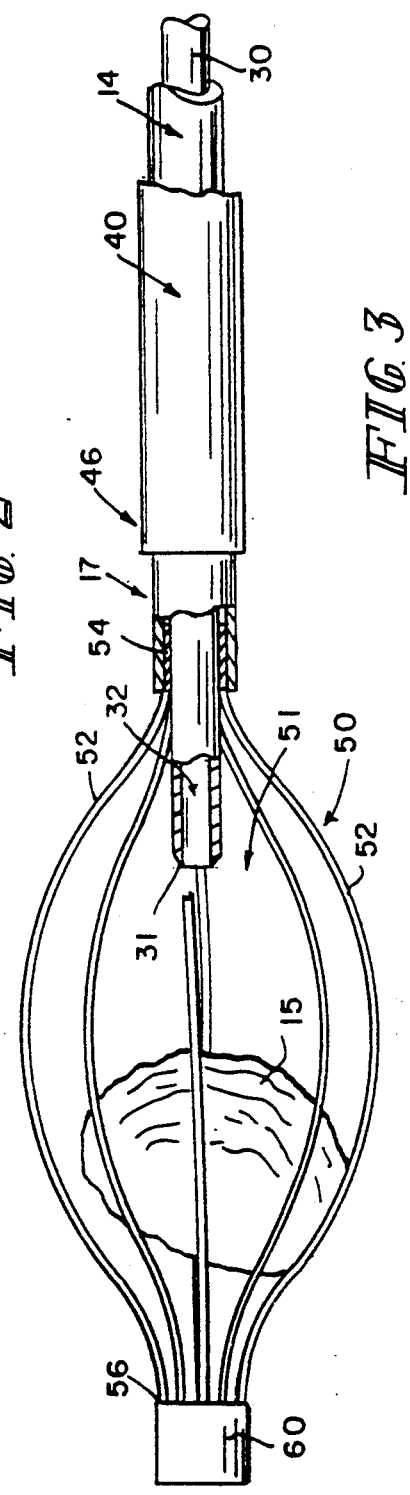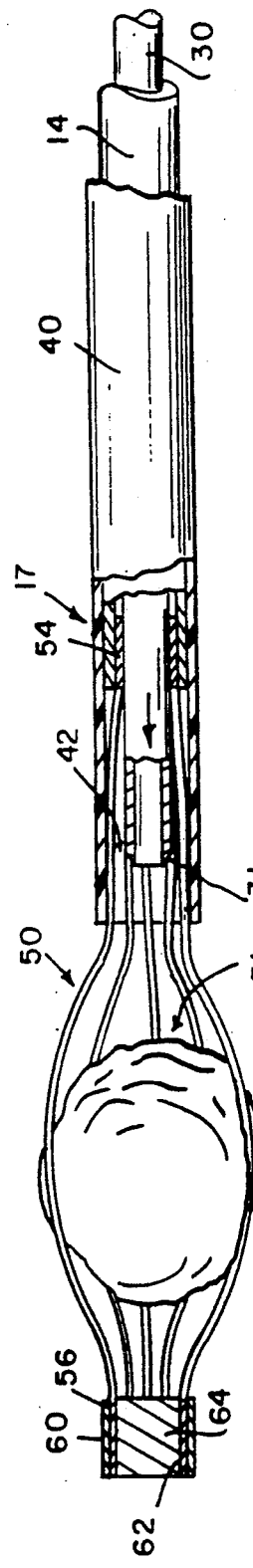

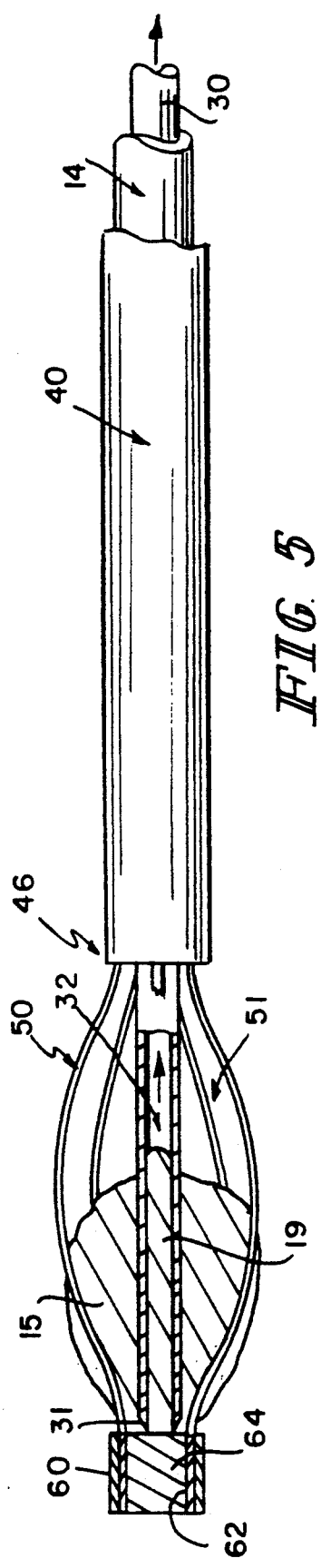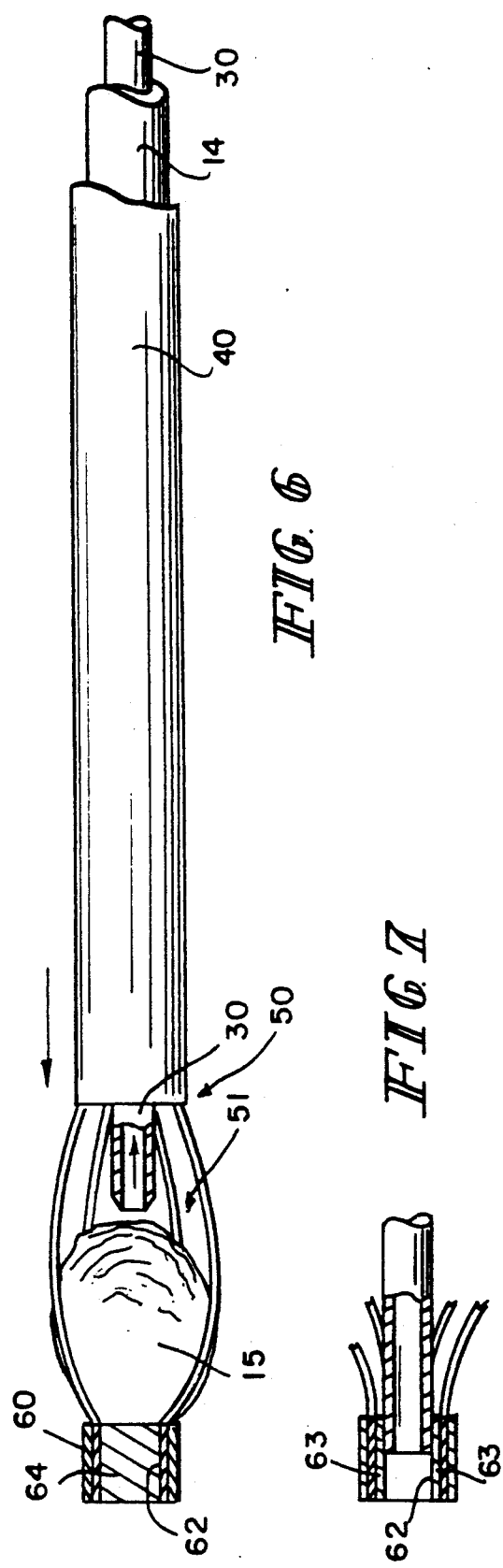

DISPOSABLE TISSUE RETRIEVAL ASSEMBLY

BACKGROUND AND SUMMARY OF THE INVENTION

The present invention relates to a tissue retrieval assembly for holding and dissecting bodily tissue. More particularly, the present invention relates to a disposable instrument useful for laparoscopic procedures. The disposable instrument has a basket for holding tissue and a cutting element for dissecting held tissue. Tissue samples cut away by the disposable instrument can be optionally held in a tissue trap container.

Laparoscopic surgery can be effectively used for removal of gall bladders, ovaries, tumors, or other body organs or tissues found in the abdominal cavity. Commonly, a cutting instrument attached to an end of a cannula is used to excise tissue. The excised tissue is then immediately sucked up through the cannula for disposal as medical waste. Alternatively, excised tissue can be grasped or held by tweezers, pincers, or other similar medical devices, and pulled out through a cannula inserted into an abdominal cavity through a laparoscopic puncture.

However, medical devices constructed for the practice of the foregoing tissue retrieval methods are not always suitable for retrieving relatively large bits of tissue, and/or small organs. Excised bits of tissue can be lost or move away from the operating site before they are sucked, grasped or pulled through a cannula. In addition, larger bits of tissue and small organs will not fit in one piece through the small diameter cannula used in laparoscopic procedures. Since the cannula diameter should be minimized to reduce patient trauma, simply providing larger cannula is not desirable.

The present invention provides an apparatus for retrieval of small organs and tissue from a patient's body. Tissue is dissected and removed from a patient with the aid of an instrument that includes a collapsible basket formed to define a basket cavity to contain tissue. Optionally, an anvil is attached to the basket to form an impacting surface. The basket can be collapsed to allow insertion of the collapsible basket into, and withdrawal from, a patient's body.

A cutting cannula, formed to define a cutting cannula cavity, is positioned to be reciprocatingly movable to pass through the basket cavity and impact the anvil. In operation, the cutting cannula is manually and reciprocatingly driven to pass into and through the basket cavity, cutting any tissue contained in the basket cavity. The cut tissue is then withdrawn from the patient and saved for analysis or disposed of as medical waste.

In preferred embodiments, the collapsible basket includes a plurality of flexible members. Each flexible member has a first and a second end and is prestressed to define an arcuate shape between its first and second ends. The first end of each flexible member is attached to a support tube positioned to surround the cutting cannula, and the second end of each flexible member is attached to the anvil. With this attachment arrangement the anvil is supported and the basket cavity is defined between the support tube and the anvil.

In preferred embodiments, a shield tube is positioned to surround the support tube, and the shield is movable forward over the basket to straighten and effectively collapse the flexible members forming the basket. Withdrawal of the shield tube from contact with the flexible members allows recovery of their arcuate shape and reformation of the basket cavity.

In another preferred embodiment, the cutting cannula is reciprocatingly moved with the aid of a support tube attached to hold the basket, a handle attached to the support arm, and a lever arm attached to the cutting cannula. The lever arm is biasingly connected to the handle (typically by a hinge/spring system) so that operational movement of the lever arm relative to the handle moves the cutting cannula toward the anvil. A biasing element, such as a spring, is connected to move the lever arm away from the handle to encourage reciprocating motion of the cutting cannula. The cavity of the cutting cannula is attached in fluid connection to a vacuum source.

The present invention also encompasses a method for dissecting and removing tissue from a patient's body. The method includes the steps of entrapping tissue in a collapsible basket formed to define a basket cavity, providing an anvil attached to the basket, and cutting tissue trapped in the basket by reciprocating motion of a cutting cannula, the cutting cannula being movable to pass through the basket cavity and impact the anvil, cutting any tissue contained in the basket cavity. Any cut tissue is contained in the cutting cannula cavity is withdrawn for analysis or disposal.

BRIEF DESCRIPTION OF THE DRAWINGS

FIG. 2 illustrates a working end, normally inserted into a patient's abdomen, of the disposable instrument as shown in FIG. 1. A basket attached to a support tube at one end is shown collapsed by movable shield tube concentrically disposed to fit over the support tube and the basket;

FIG. 3 illustrates the basket, fully expanded after withdrawal of the shield tube, with each prestressed flexible strip composing the basket being attached to the support tube and to an anvil;

FIG. 4 shows the shield tube moving forward to partially collapse the basket and closely entrap and hold a tissue sample;

FIG. 5 shows a cutting cannula reciprocally positioned in the support tube, with the cutting cannula extending out from the working end of the support tube to pass through the basket and impact the anvil, cutting a core out of the tissue contained in the basket;

FIG. 6 shows the cutting cannula retracted and the shield tube moved forward to compress the basket and to firmly hold the tissue sample; and FIG. 7 illustrates an anvil having no central plug to allow a conformably dimensioned cutting cannula to slide into an anvil cavity, cutting away any contained tissue sample.

DETAILED DESCRIPTION OF THE INVENTION

Figure 1:
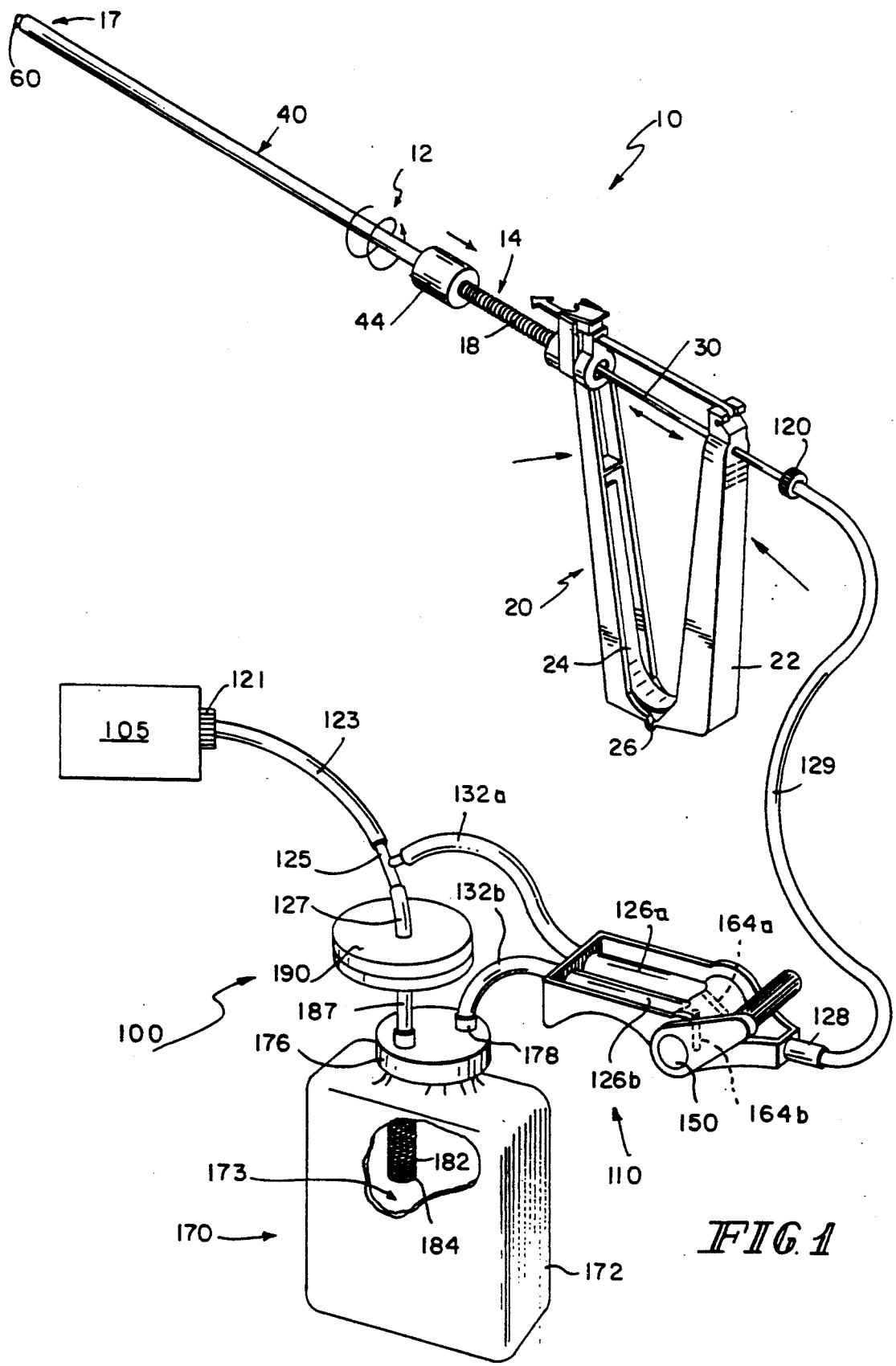
FIG. 1 is a perspective view of a tissue retrieval assembly that includes a disposable instrument connected to a vacuum source. A tissue sample trap for retention of tissue extracted with the aid of the disposable instrument is shown.

As illustrated in FIG. 1, a tissue retrieval assembly 10 includes a disposable instrument 12 in fluid connection with a tissue sample trap system 100 and vacuum source 105. The disposable instrument 12 includes a support tube 14, with the support tube 14 having a working end 17 that is inserted into a patient's body for dissection and removal of the tissue. The support tube 14 internally defines a support tube cavity 16 and externally defines threads 18. Preferably, the support tube is 14 is constructed from tubular surgical steel, aluminum, or other rigid, biocompatible metal. Alternatively, substantially rigid thermoset plastics such as polyethylene, polypropylene, or polycarbonates can be used. In the embodiment illustrated, the support tube cavity 16 is formed to have a substantially circular cross section (taken perpendicular to the longitudinally extending tube 14), but alternative cross sections such as elliptical, rectangular, square, etc., are also contemplated. In the illustrated embodiment, the support tube 14 has a diameter of about 6 mm, but the diameter can typically range from about 4 mm to about 12 mm or more.

The support tube 14 is connected to a handle 20 that can be held by a surgeon or other medical personnel operating the disposable instrument 12. Concentrically disposed within the support tube cavity 16 is a cutting cannula 30. The cutting cannula 30 internally defines a cutting cannula cavity 32 and has a sharpened cutting tip 31. Like the support tube 14, the cutting cannula 30 is typically constructed from tubular surgical steel, aluminum, or other rigid, biocompatible metal. Alternatively, substantially rigid thermoset plastics such as polyethylene, polypropylene, or polycarbonates can be used. If plastics are used to form cutting cannula 30, however, the sharpened cutting tip 31 of the cutting cannula 30 is generally tipped with sharp edged metal to enhance its cutting efficacy. In the embodiment illustrated, the cutting cannula cavity 32 is formed to have a substantially circular cross section (taken perpendicular to the cannula 30), but alternative cross sections such as elliptical, rectangular, square, etc. can also be used. In the illustrated embodiment, the cutting cannula 30 has a diameter of about 5 mm, but the diameter can typically range from about 2 mm to about 12 mm or more. subject to the limitation that the cutting cannula 30 must fit within the support tube cavity 16.

The cutting cannula 30 is concentrically disposed for reciprocal movement within the support tube cavity 16. The cutting cannula 30 is attached to the lever arm 22. The lever arm 22 is connected to the handle 20 by a hinge 26 and a spring 24. The spring 24 is formed from a single piece of strip steel that is bent and positioned between the handle 20 and the lever arm 22. The force exerted by the spring 24 acts to force apart the handle 20 from the lever arm 22.

In operation, an operator of the disposable instrument 12 simultaneously grasps the handle 20 with fingers of a hand and also grasps the lever arm 22 with the thumb and palm of the hand. Bringing the thumb and fingers together with sufficient force to overcome the biased force exerted by spring 24 causes the lever arm 22 to move closer to the handle 20. This in turn causes movement of the attached cutting cannula 30 toward and out from the working end 17 of the support tube 14. The biased force of spring 24 is then allowed to force apart the lever arm 22 and the handle 20 as the grip of the operator is relaxed. The cutting cannula 30 is withdrawn into the support tube cavity 16 and the operator of the instrument 12 can repeat the cycle of grip/release to drive the cutting cannula 30 out of and into the support tube cavity 16.

Although imparting reciprocating movement to the cutting cannula 30 is simple and effective with the above described lever arm mechanism, alternative embodiments having different reciprocating mechanisms are also contemplated. For example, tension or compression springs, rather than strip springs can be used to force the lever arm 22 apart from the handle 20. In other embodiments, no biasing mechanism is used at all, with an operator directly pushing and pulling a cutting cannula. Alternatively, other mechanical drives such as screw mechanisms, pneumatic drives, vacuum drives, or electrical mechanisms can be used to drive the cutting cannula forward and backward through the support tube 14. In addition to manual operation, automatic and semi-automatic mechanisms that drive the cutting cannula are contemplated within the scope of this invention.

A shield tube 40, formed to define a shield tube cavity 42, is concentrically disposed about the support tube 14. The shield tube 40 is connected to a threaded adapter 44 for engaging in threaded connection the threads 18 externally defined on the support tube 14. Screwing motion applied to either the shield tube 40 or the threaded adapter 44 allows an operator to move the shield tube longitudinally along the support tube 14 either toward the working end 17 or away from the working end 17, toward the handle 20.

Like both the cutting cannula 30 and the support tube 14, the shield 40 is preferably constructed from tubular surgical steel, aluminum, or other rigid, biocompatible metal. Alternatively, substantially rigid thermoset plastics such as polyethylene, polypropylene, or polycarbonates can be used to form the shield 40. In the illustrated embodiment, the shield 40 has a diameter of about 7 mm, but the diameter can typically range from about 5 mm to about 12 mm or greater, subject to the limitation that it must fit over the support tube 14.

As shown in FIGS. 2-6, a basket 50 composed of a plurality of flexible strips 52, is used to entrap and hold tissue in a basket cavity 51 Each of the flexible strips 52 have first ends 54 and second ends 56. The first ends 54 are attached to the working end 17 of the support tube 14. The second ends 56 of the flexible strips 52 are attached to an anvil 60. Optionally, the ends 56 can be directly attached to each other (e.g. by welding attachment) to form a basket (not shown). The flexible strips are formed from surgical steel, and are prestressed to assume an arcuate, smoothly curving shape between their respective first and second ends when not constrained by the shield tube 40.

In their fully expanded position, the plurality of flexible strips 52 define a roughly spherical basket 50 such as illustrated in FIG. 4. The flexible strips 52 can move slightly apart from each other to accommodate passage of tissue 15 from a patient into the basket cavity 51. Movement of the shield tube 40 forward over the basket 50 causes the basket 50 to gradually collapse, reducing the volume of the basket cavity 51 and straightening the flexible strips 52. A partially collapsed basket 50 is best illustrated in FIGS. 4 through 6. Completely covering the basket 50 with the shield 40 (as shown in FIG. 2) facilitates insertion of the basket 50 into a patient, and retraction of the shield 40 allows capture of tissue in the basket cavity 51.

Tissue or organs captured in the basket cavity are cut into smaller pieces by action of the cutting cannula 30 moving forward to compress tissue 15 between itself and the anvil 60. As illustrated in FIGS. 1-6, the anvil 60 is constructed of surgical steel to define a tubular cavity 62. A solid plug is inserted into the tubular cavity 62 to provide a solid impacting surface against which the cutting cannula 30 can be contacted. Preferably, the plug is constructed from rigid polymeric material such as polyethylene and permanently force fitted into the cavity 62.

In alternative embodiments, such as illustrated in FIG. 7, the tubular cavity 62 and the cutting cannula 30 are dimensioned to allow the cutting cannula 30 to conformably slide into the tubular cavity 62 of the anvil 60. A sleeve 63 can be inserted into the tubular cavity 62 of the anvil 60 to allow a conforming fit with the cutting cannula 30. In operation, the cutting cannula 30 will force tissue 15 into the tubular cavity 62 as it moves toward the anvil 60, and cut that tissue away from the main tissue mass as the cutting cannula 30 moves into the cavity 62.

Tissue "cores" cut away from tissue 15 by the slicing impact action of the cutting cannula 30 against the anvil 60 can be removed by suction applied through the cutting cannula cavity 32. As shown in FIG. I, the cutting cannula cavity is in fluid communication with vacuum source 105 by way of tissue sample trap system 100. The tissue sample trap system 100 allows recovery for analysis or disposal of the tissue sample core cut away by the cutting cannula 30. As illustrated in FIG. 1, the tissue sample trap system 100 includes a dual valve 110, similar to the valve described in FIG. 10 of U.S. Pat. No. 5,019,054, issued May 28, 1991 to Clement et al., the disclosure of which is herein incorporated by reference. The system 100 includes a valve 110 connected to container 170 for holding tissue samples (not shown). The valve 110 is formed to define first and second passageways 126a and 126b. The passageways 126a and 126b are alternately operably connected in fluid communication with a third passageway 128 defined in the valve 110. A rotor 150, formed to define two transaxial passageways 164a and 164b, can be rotated between a first position in which passageway 164a connects in fluid communication third passageway 128 and first passageway 126a, and a second position (not illustrated) in which passageway 164b connects in fluid communication third passageway 128 and second passageway 126b.

The third passageway 128 is also in fluid connection with conduit 129. Conduit 129 is formed of a flexible plastic and terminates in an adaptor 120 for mating connection with surgical instruments, lavages, cannulas, or other devices for retrieving bodily fluids and tissues. In alternative embodiments, the valve 110 can be fitted with an integral conduit piece (not shown) to aid in retrieval of fluid and tissue samples from a patient.

The first passageway 126a is connected through conduit 132a, T-conduit 125, conduit 123 and vacuum adaptor 121 to a standard medical vacuum source (not shown). When the valve is in the first position as shown in FIG. 1, the suction of a vacuum source draws fluid or tissue through the cutting cannula cavity 32 of the instrument 12 into conduit 129, through passageways 128, 164a, and 126a of the valve 110, and through conduits 132a, 125, and 123. Tissue or fluids drawn from the patient through this pathway are normally discarded without analysis.

When analysis of fluid or tissue samples is desired, the rotor 150 can be rotated by an operator to break the fluid connection between the third passageway 128 and first passageway 126a, and bring the third passageway 128 into fluid communication with the second passageway 126b. The second passageway 126b is connected in fluid communication with a chamber 173 by a conduit 132b. The chamber 173 is defined by a container wall 172 and holds tissue or fluid samples. The conduit 132b connects to a nipple 178 formed in a cap 176 that is screwed onto the container 170. Since the chamber 173 of the container 170 is also in fluid connection with the vacuum source by way of conduits 187, 127, 125, and 123, liquid or tissue samples are drawn by suction (inflow) into the chamber 173 of container 170.

Continued passage (outflow) of liquid or tissue samples through conduits 187, 127, and 123 is inhibited by placement of filters that block or obstruct passage of the sample As illustrated by the broken-away portion of the container 170 in FIG. 1, a filter screen 182 is positioned in the chamber 173. The filter screen 182 is formed to define a plurality of apertures 184 that permit withdrawal of air from chamber 173 through conduits 187, 127, 123, but prevent passage (outflow) of tissue samples sized larger than the apertures 184. A secondary, in-line filter 190 is also connected between conduits 187 and 127 to reduce passage of samples into conduit 127 and trap small bits of tissue or fluid.

In operation, a surgeon or other medical personnel simply rotates the rotor 150 from its first position with tissue passing directly to the vacuum source, to its second position, so that tissue samples are trapped in the container 170. The tissue sample containing container 170 can be disconnected (by unscrewing the cap 176) from the system 100 and taken for laboratory analysis. The remaining, now contaminated, elements of the system 100 are then disposed of by approved medical waste disposal procedures.

Operation of the tissue retrieval assembly 10 involves removal of the disposable instrument 12 and tissue sample trap system 100 from a sealed and sterile package (not shown). The system 100 is connected to vacuum source 105 with the vacuum adaptor 121. Initially the rotor 150 of the dual valve is turned to allow direct passage of tissue samples from the disposable instrument 12 to the vacuum source, or alternatively the rotor is turned to block any fluid passage between either passages 126a and 126b and third passageway 128.

The surgeon inserts the disposable instrument into a patient's abdomen, with the basket 50 fully folded as seen in FIG. 2. As best seen in FIG. 3, the shield tube 40 is retracted, allowing the prestressed flexible strips 52 to assume their arcuate shape and collectively define the basket cavity 51. The surgeon maneuvers the basket 50 to capture tissue 15, and then proceeds to move the shield tube 40 forward to reduce the volume of the basket cavity 51 and closely hold the tissue 15 in place as best seen in FIG. 4.

The surgeon then operates the lever arm 22 to move the cutting cannula 30 forward into the basket cavity 51 to impact the anvil 60. This action cuts a tissue core 19, as seen in FIG. 5. Upon separation from the tissue 15, the tissue core 19 is drawn through the cutting cannula cavity 32 and either directly passes to the vacuum source 105, or more typically, is captured by the container 170 of the tissue sample trap system 100. As the tissue 15 is reduced in size, the shield 40 is moved forward, as shown in FIG. 6, to keep the tissue 15 tightly held. The process of moving the shield 40 forward, followed by cutting action with the cutting cannula 30, is repeated until the tissue 15 is removed from the basket cavity 51. The instrument 12 is then removed from the patient's body cavity and disposed of as medical waste. Tissue samples retrieved and held by the system 100 are stored or removed for analysis.

I claim:

1. An instrument for dissecting and removing tissue from a patient's body, the instrument comprising a collapsible basket formed to define a basket cavity to contain tissue, the collapsible basket being positionable in a patient's body to entrap said tissue, means attached to the collapsible basket for collapsing the collapsible basket to allow insertion of the collapsible basket into a patient's body, a cannula having means for cutting tissue at its distal end, the cutting means being movable to pass through the means for collapsing the basket to a distal end of the collapsible basket and to cut any tissue contained in the basket cavity, means attached to the cutting means for moving the cutting means to cut tissue, and means connected to the basket cavity for withdrawing cut tissue from the basket cavity.

2. The instrument of claim 1, wherein the collapsible basket further comprises a plurality of flexible members, each flexible member having a first and a second end, and each flexible member being prestressed to define an arcuate shape between its first and second ends.

3. The instrument of claim 2, wherein the second end of each flexible member is attached to an anvil and further comprising a support tube positioned to surround the cutting means, with the first end of each flexible member being attached to the support tube.

4. The instrument of claim 3, wherein the collapsing means further comprises a shield tube positioned to surround the support tube, and means for alternately moving the shield tube to straighten and effectively collapse said flexible members forming the basket and to withdraw the shield tube from contact with the flexible members to allow recovery of their arcuate shape and formation of the basket cavity.

5. The instrument of claim 1, wherein an anvil is attached to the collapsible basket to form an impacting surface for the cutting means.

6. The instrument of claim 5, wherein the anvil defines a tubular cavity dimensioned to conformably accept the cutting means.

7. The instrument of claim 6, wherein a solid plug is inserted into the tubular cavity to provide a solid impact surface for the cutting means.

8. The instrument of claim 5, wherein the moving means further comprises a support tube attached to hold the collapsible basket, a handle attached to the support tube, a lever arm attached to the cutting means, and means for biasingly connecting the lever arm to the handle so that operational movement of the lever arm relative to the handle moves the cutting means toward the anvil.

9. The instrument of claim 8, wherein the biased connecting means includes a hinge attaching the lever arm to the handle and a spring biased to urge separation of the lever arm from the handle.

10. The instrument of claim 1, wherein the withdrawing means further comprises means for providing a fluid connection between the basket cavity and a vacuum source.

11. An instrument for dissecting and removing tissue, the instrument comprising a support tube formed to define a support tube cavity therethrough, the support tube having a working end insertible into a patient's body, a shield tube concentrically positioned to surround the support tube, a basket defining a basket cavity for holding tissue, the basket being formed from a plurality of flexible strips, each flexible strip having first and second ends, and with the first end of each flexible strip attached to the working end of the support tube, an anvil attached to the second end of each of the plurality of flexible strips to further define the basket cavity, a cutting cannula means reciprocatingly movable in the support tube cavity, the cutting cannula being extendable from the working end of the support tube to pass through the basket cavity and impact the anvil, cutting any tissue contained in the basket cavity, means for reciprocatingly moving the cutting cannula means, and means for moving the shield tube relative to the support tube to alternately collapse and allow expansion of the basket.

12. The instrument of claim 11, wherein the reciprocating moving means further comprises a handle attached to the support tube, a lever arm attached to the cutting cannula means, and means for biasingly connecting the lever arm to the handle so that operational movement of the lever arm relative to the handle moves the cutting cannula means toward the anvil.

13. The instrument of claim 12, wherein the biased connecting means includes a hinge attaching the lever arm to the handle and a spring biased to urge separation of the lever arm from the handle.

14. The instrument of claim 11, wherein the instrument also comprises a withdrawing means for providing a fluid connection between the collapsible basket cavity and a vacuum source for removing tissue contained in the basket cavity.

15. The instrument of claim 11, wherein the support tube is formed to define external threads, and further comprising means for engaging the external threads of the support tube, the engaging means being attached to the shield tube.

16. A method for dissecting and removing tissue from a patient's body, the method comprising the steps of entrapping tissue in a collapsible basket formed to define a basket cavity, providing an anvil attached to the basket, cutting tissue trapped in the basket cavity by movement of a cutter, wherein the cutter moves to pass through the basket cavity and impacts the anvil, cutting any tissue contained in the basket cavity, and withdrawing cut tissue contained in the basket cavity.

17. A tissue sample trap system, the system comprising a collapsible basket formed to define a basket cavity to contain tissue, said collapsible basket having an anvil at an end thereof, means for collapsing the basket to allow insertion of the collapsible basket into a patient's body, a cutter means formed to define a cutting cavity, the cutter being movable to pass through the means for collapsing the basket and impact the anvil, cutting any tissue contained in the basket cavity, means for moving the cutter to cut tissue, and a valve body shaped to be gripped and securely held while leaving a thumb free for valve operational movement, said body providing first and second passageways alternately in fluid communication with a third passageway positioned in fluid communication with the cutting cavity, said valve body also formed to define a cylindrical opening extending transversely therethrough and in fluid communication with said passageways, a cylindrical rotor for snug slidable and rotational insertion into said cylindrical opening, the rotor having two transaxial passageways therethrough to provide alternate fluid communication between the first passageway and the third passageway, and the second passageway and the third passageway, and thumb-actuated means for rotating said rotor, an airtight container formed to define a chamber for holding tissue samples, inflow means for connecting one of the first or second passageways of the valve body to the container in airtight fluid communication, and outflow conduit means for connecting the container in fluid communication to a vacuum source to withdraw tissue samples from the basket cavity through the cutter cavity, the third passageway, one of the transaxial passageways, one of the first or second passageways to said air tight container.

18. The system of claim 17, wherein the first passageway is connected to the vacuum source and the second passageway is connected to the inflow means.

19. The system of claim 17, wherein the outflow conduit means further comprises filtering means to prevent passage of tissue samples from the container through the outflow conduit means.

20. The system of claim 19, wherein the filtering means comprises a filter screen positioned in the chamber of the container, the filter screen being in fluid communication with the outflow conduit means, and having a plurality of apertures therethrough to allow passage of air and reduce admittance of tissue into the outflow conduit means.

* * * * *